US011253553B1

(12) United States Patent
Ha

(10) Patent No.: US 11,253,553 B1
(45) Date of Patent: Feb. 22, 2022

(54) COMPOSITION FOR IMPROVING COGNITIVE ABILITY AND PREVENTING OR TREATING DEMENTIA AND ATTENTION DEFICIT HYPERACTIVITY DISORDER, COMPRISING GALLA RHOIS EXTRACT AND FRAXIN AS ACTIVE INGREDIENTS

(71) Applicants: Sang Hee Kim, Seoul (KR); Hyun Kee Kim, Seoul (KR)

(72) Inventor: Seon Ah Ha, Seoul (KR)

(73) Assignees: Sang Hee Kim, Seoul (KR); Hyun Kee Kim, Seoul (KR)

( * ) Notice: Subject to any disclaimer, the term of this patent is extended or adjusted under 35 U.S.C. 154(b) by 0 days.

(21) Appl. No.: 17/299,227

(22) PCT Filed: Dec. 18, 2018

(86) PCT No.: PCT/KR2018/016129
§ 371 (c)(1),
(2) Date: Jun. 2, 2021

(87) PCT Pub. No.: WO2020/130172
PCT Pub. Date: Jun. 25, 2020

(51) Int. Cl.
*A61K 35/64* (2015.01)
*A61P 25/00* (2006.01)
*A61K 31/704* (2006.01)

(52) U.S. Cl.
CPC ............ *A61K 35/64* (2013.01); *A61K 31/704* (2013.01); *A61P 25/00* (2018.01)

(58) Field of Classification Search
None
See application file for complete search history.

(56) References Cited

U.S. PATENT DOCUMENTS

| 6,010,702 A | 1/2000 | Lee et al. |
| 2004/0152760 A1 | 8/2004 | Castillo et al. |

FOREIGN PATENT DOCUMENTS

| CN | 108348557 A | 7/2018 |
| KR | 1999-0085202 A | 12/1999 |
| KR | 20040021882 A | 3/2004 |
| KR | 10-2011-0110638 A | 10/2011 |
| KR | 10-1147486 B1 * | 5/2012 |
| KR | 10-2013-0108821 A | 10/2013 |
| KR | 10-2014-0021882 A | 2/2014 |
| KR | 20140022941 A | 2/2014 |
| KR | 10-1414988 B1 | 7/2014 |
| KR | 10-2235881 B1 | 4/2021 |
| KR | 10-2246444 B1 | 4/2021 |
| WO | WO-2019109300 A1 | 6/2019 |
| WO | WO-2019225983 A1 | 11/2019 |

OTHER PUBLICATIONS

International Search Report from corresponding PCT Application No. PCT/KR2018/016129, dated Sep. 6, 2019.
Whang, Wan Kyunn et al., Natural compounds, fraxin and chemicals structurally related to fraxin protect cells from oxidative stress. Experimental and Molecular Medicine. Oct. 2005, vol. 37, No. 5, pp. 436-446.
Office Action from corresponding Korean Patent Application No. 10-2020-7034449, dated Feb. 14, 2021.
Office Action from corresponding Korean Patent Application No. 10-2021-7005138, dated Mar. 22, 2021.
Allowed Claims of corresponding KR 10-2246444 B1, 2021.
Allowed Claims of corresponding KR 10-2235881 B1, 2021.
Office Action from Japanese Patent Application No. 2021-535156 dated Nov. 24, 2021.
Office Action from Chinese Patent Application No. 2021110901979050 dated Nov. 12, 2021.
Examiner Search Report from Great Britain Patent Application No. 2114517.2 dated Oct. 25, 2021.
Chen mei hua, et al., Protective effects of fraxetin on cerebral ischemia-reperfusion injury in rats, Tai San medical sciences & pharmacy institutes, Shan Dong Tai An, 1005-9202 (2016).
Zheng, Xue-Hua et al. "Research progress on pharmacological effects of gallic acid" Chin Hosp Pharm J, Jan. 2017, vol. 37, No. 1.
Jiang, Rui et al. "Fraxetin alleviates cell injury through the inhibition of NF-$_k$B/COX- 2" Journal of Shenyang Pharmaceutical University vol. 34, No. 6, Jun. 2017.

* cited by examiner

*Primary Examiner* — Susan Hoffman
(74) *Attorney, Agent, or Firm* — Harness, Dickey & Pierce, P.L.C.

(57) ABSTRACT

The present invention relates to a composition for improving cognitive ability, and preventing or treating dementia and a hyperactivity disorder, which includes a *Galla rhois* extract and fraxin as active ingredients. It was identified that the composition including the *Galla rhois* extract and fraxin significantly improves cognitive memory in an Alzheimer's disease model induced by Aβ (1-42) administration and an APPswe/PS1dE9 double-expressing Alzheimer's disease model, and inhibits the generation of amyloid plaques, suggesting the usefulness of the combination of the *Galla rhois* extract and fraxin, as a therapeutic material, against Alzheimer's disease, and showing that the combination of the *Galla rhois* extract and fraxin is able to be used as a therapeutic agent for ADHD.

2 Claims, 13 Drawing Sheets

COMPOSITION FOR IMPROVING COGNITIVE ABILITY AND PREVENTING OR TREATING DEMENTIA AND ATTENTION DEFICIT HYPERACTIVITY DISORDER, COMPRISING GALLA RHOIS EXTRACT AND FRAXIN AS ACTIVE INGREDIENTS

CROSS-REFERENCE TO RELATED APPLICATIONS

This application is a national phase application of PCT Application No. PCT/KR2018/016129, filed on 18 Dec. 2018. The entire disclosure of the application identified in this paragraph is incorporated herein by reference.

TECHNICAL FIELD

The present invention relates to a composition for improving cognitive ability, and preventing or treating dementia and attention deficit hyperactivity disorder, which comprises a *Galla rhois* extract and fraxin as active ingredients.

BACKGROUND ART

The decline in cognitive ability, that is, memory loss, due to dementia may be referred to as a "syndrome" in which temporary or continuous damage to cranial nerves, which mainly occur due to medical or neurological causes, results in remarkable difficulty in maintaining social and daily life.

Alzheimer's disease accounts for the majority of patients with dementia. The pathogenesis of Alzheimer's disease is not yet clearly identified, but the toxicity of a neurotoxic protein (β-amyloid protein) deposited in a brain lesion is suggested as the most important cause.

Alzheimer's disease and cerebrovascular dementia caused by extensive brain lesions generated after stroke or due to cerebral arteriosclerosis accounts for approximately 90% of dementia diseases.

Dementia patients exhibit significant hypofunction of various neurotransmitters mainly in the cerebral cortex and limbic system and hypofunction of cerebral energy metabolism, and particularly, in the case of Alzheimer's disease (AD), the hypofunction of acetylcholine (ACh), glutamic acid, neuropeptide and monoamine neurotransmission systems was exhibited in patients, assuming that the dysfunction of these neurotransmission systems is the main cause of AD.

In addition, from the aspect of the neurocytotoxic action induced by a β-amyloid peptide, the onset mechanism mediated by detachment of hippocampal nerve cells through extracellular deposition of β-amyloid peptides in senile plaques is also assumed as one of the main causes of AD.

Currently, the treatment of dementia aims to lower progression by early diagnosis of symptoms, and there is no drug that can inhibit or prevent the progression of dementia at the present stage. While there are Cogne (Parke-Davis), Aricept (Eisai & Pfizer), Exellon (Novartis) and Ebixa (Lundbeck), which are products having been approved by the U.S. FDA and available on the market, these drugs except Ebixa only contribute to alleviation of some of the symptoms generated by AD (to increase the concentration of a neurotransmitter, i,e, acetylcholine, and its degradation enzyme, i.e., acetylcholine exterase are inhibited) and reassuring patients and their caregivers.

These AChE inhibitory drugs are most effective when the cholinergic nerve is not functionally damaged, and since their efficacy decreases with a decline in cholinergic nerve function, the drugs are only effective in the early stages of mild or moderate senile dementia. Most of these drugs exhibit cholinergic side effects of peripheral nerves, and have a very short half-life and a serious side effect such as hepatotoxicity. Particularly, when 9-amino-1,2,3,4-tetrahydroacridine (THA), which is an active ingredient of Cognex, is orally administered, it shows an improvement in perceptive ability, but is accompanied by serious side effects such as tremors, dizziness and hepatotoxicity, and thus it is not widely used.

Meanwhile, as herbal medicines not exhibiting the disadvantages of such an AChE inhibitory drug, products which include ginseng as a main ingredient and are prepared by extracting a mixture of multiple herbal medicines are disclosed in Korean Unexamined Patent Application No. 99-85202 and U.S. Pat. No. 6,010,702. Although such a herbal medicine mixed extract exhibits a certain degree of efficacy on senile dementia, it still does not guarantee definite and stable effects due to having side effects.

Meanwhile, it is estimated that attention deficit hyperactivity disorder (ADHD) occurs in 3 to 5% of school children. Psychopharmacological agents that have been proposed for treatment of this disease so far include stimulating compounds (amphetamine and methylphenidate), tricyclic antidepressants (imipramine and amitriptyline) and antipsychotics (phenothiazine and haloperidol). Methylphenidate has been proven to be effective in treatment of hyperactivity and attention deficit, and has been the target of a variety of medical studies. However, hypertension has been reported as a side reaction, and it has been shown that impulsiveness sometimes increases. In treatment with methylphenidate, frequent side effects such as black circles around eyes, enlarged pupils, headache, and the loss of appetite have been reported.

SUMMARY

Technical Problem

To solve the above-described problems, the present invention is directed to providing a novel composition for preventing or treating dementia (AD).

The present invention is also directed to providing a composition for preventing or treating attention deficit hyperactivity disorder (ADHD).

Technical Solution

To attain the purposes described above, the present invention provides a composition for preventing or treating dementia, which comprises a *Galla rhois* extract and fraxin as active ingredients.

The present invention also provides a composition for preventing or treating attention deficit hyperactivity disorder, which comprises a *Galla rhois* extract and fraxin as active ingredients.

The present invention also provides a composition for improving cognitive ability, which comprises a *Galla rhois* extract and fraxin as active ingredients.

In one embodiment of the present invention, the concentration of fraxin is preferably 0.1 to 0.5 mM, but the present invention is not limited thereto.

The composition of the present invention may be provided as a pharmaceutical composition. The pharmaceutical composition according to the present invention may further comprise a carrier, an excipient and a diluent, which are conventionally used and suitable for preparing a pharmaceutical composition. A pharmaceutical administration form of the composition of the present invention may also be used in the form of a pharmaceutically acceptable salt thereof, or used alone, or assembled or properly combined with another pharmaceutically active compound. The salt may be any salt that is pharmaceutically available without particular limitation, and may include, for example, hydrochloric acid, sulfuric acid, nitric acid, phosphoric acid, hydrofluoric acid, hydrobromic acid, formic acid, acetic acid, tartaric acid, lactic acid, citric acid, fumaric acid, maleic acid, succinic acid, methanesulfonic acid, benzenesulfonic acid, toluenesulfonic acid, and napthalenesulfonic acid.

The pharmaceutical composition according to the present invention may be formulated in any form suitable for a pharmaceutical preparation, including oral formulations such as a powder, a granule, a tablet, a capsule, a suspension, an emulsion, a syrup and an aerosol, preparations for external use such as an ointment and a cream, a suppository and a sterile injectable solution, according to conventional methods.

In the pharmaceutical composition according to the present invention, a preferable dose of the extract or compound of the present invention may vary according to a subject's age, sex and body weight, symptoms, the severity of a disease, a dosage form, and the route and duration of administration. However, for preferable effects, the composition of the present invention is preferably administered daily at 0.001 to 500 mg/kg of body weight. The daily dose may be administered once or in divided portions. In addition, the dose may be increased or decreased according to age, sex, a body weight, the severity of a disease or the route of administration. Therefore, the dose does not limit the scope of the present invention in any way.

The pharmaceutical composition according to the present invention may be administered into mammals such as rats, mice, livestock or humans in various routes, for example, parenteral or oral routes, and all types of administration may be expected, for example, by oral, intrarectal, intravenous, muscular, subcutaneous, intrauterine or intracerebroventricular injection.

In addition, the composition of the present invention may be provided as a food additive or functional food composition. The food composition according to the present invention may include, for example, all kinds of foods such as chewing gums, caramels, candies, ice creams and confectioneries, beverages such as soft drinks and mineral water, and health functional foods such as vitamins and minerals.

Here, the content of the extract or compound may be 0.001 to 99.9 wt % of the total weight of food in food, and 0.001 to 0.1 g per 100 mL in beverages.

The beverage of the present invention has no limit on components except that it contains the extract and compound as essential components at a predetermined ratio, and may contain additional components such as various flavors or natural hydrocarbons like conventional beverages.

Other than these components, the health functional food composition of the present invention may contain a variety of nutrients, vitamins, minerals (electrolytes), flavoring agents including synthetic and natural flavoring agents, coloring agents and fillers (cheese, chocolate, etc.), pectic acid and a salt thereof, alginic acid and a salt thereof, an organic acid, protective colloid thickening agents, pH modifiers, stabilizers, preservatives, glycerin, alcohols, or carbonating agents used in carbonated beverages.

Advantageous Effects

In the present invention, it was identified that a composition including a *Galla rhois* extract and fraxin significantly improves cognitive memory in an Alzheimer's disease model induced by Aβ (1-42) administration and an APPswe/PS1dE9 double-expressing Alzheimer's disease model and inhibits the generation of amyloid plaques, and this result can suggest the usefulness of the combination of the *Galla rhois* extract and fraxin, as a therapeutic agent, for Alzheimer's disease, and show that the composition of the *Galla rhois* extract and fraxin can be used as a therapeutic agent for attention deficit hyperactivity disorder (ADHD).

Figure 8:
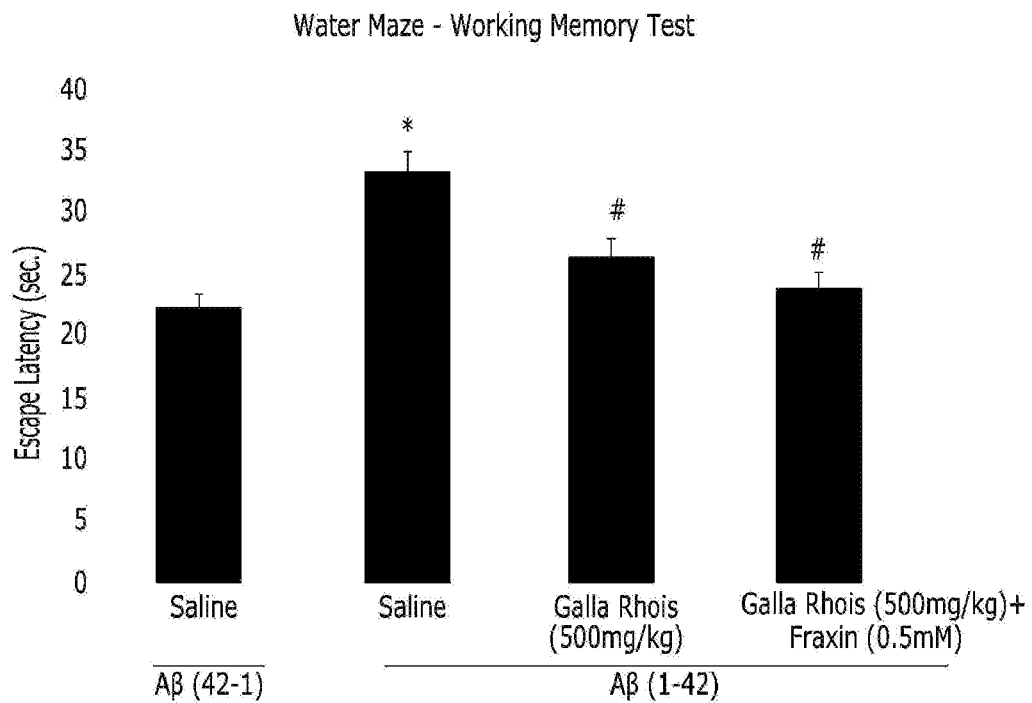

FIG. 8 shows the effect of co-administration of a *Galla rhois* ethanol extract and/or fraxin on a β-amyloid (1-42)-mediated decline in cognitive memory. Eight mice per group were measured four times a day for three days, and each value is expressed as mean±SEM. *P<0.01 vs. Saline+β-amyloid (42-1), #P<0.05, and ##P<0.01 vs. Saline+β-amyloid (1-42) (using one-way ANOVA and a Fisher's PLSD test for a post-test).

Figure 9:
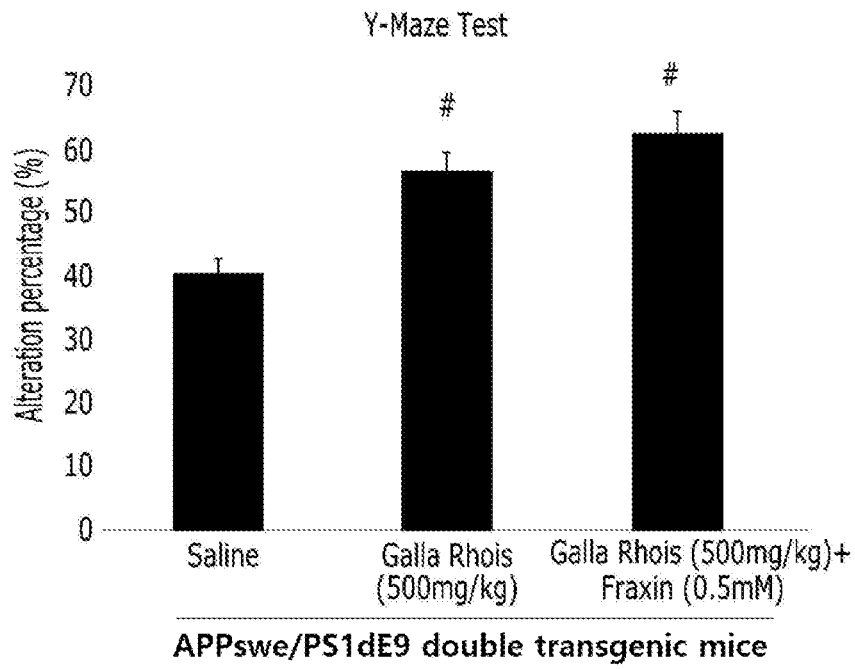

FIG. 9 shows the pharmacological effect of co-administration of a *Galla rhois* ethanol extract (*Galla rhois*) and/or fraxin on the cognitive memory (evaluated by a Y-maze test) of APPswe/PS1dE9 double-expressing mice. Each value is expressed as mean±SEM of 10 mice. #P<0.05 vs. Saline (using One-way ANOVA and a Fisher's test for a post-test).

Figure 10:
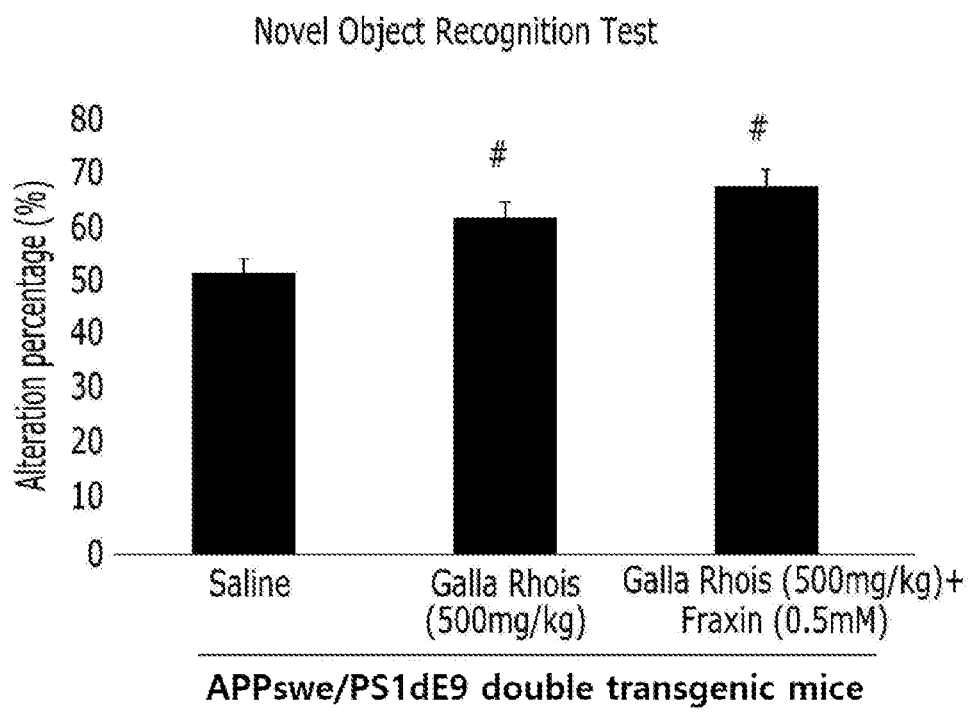

FIG. 10 shows the pharmacological effect of the co-administration of a *Galla rhois* extract (*Galla rhois*) and/or fraxin on the cognitive memory of APPswe/PS1dE9 double-expressing mice (evaluated by a novel object recognition test). Each value is expressed as mean±SEM of 10 mice. #P<0.05 vs. Saline (using One-way ANOVA and a Fisher's test for a post-test).

Figure 11:
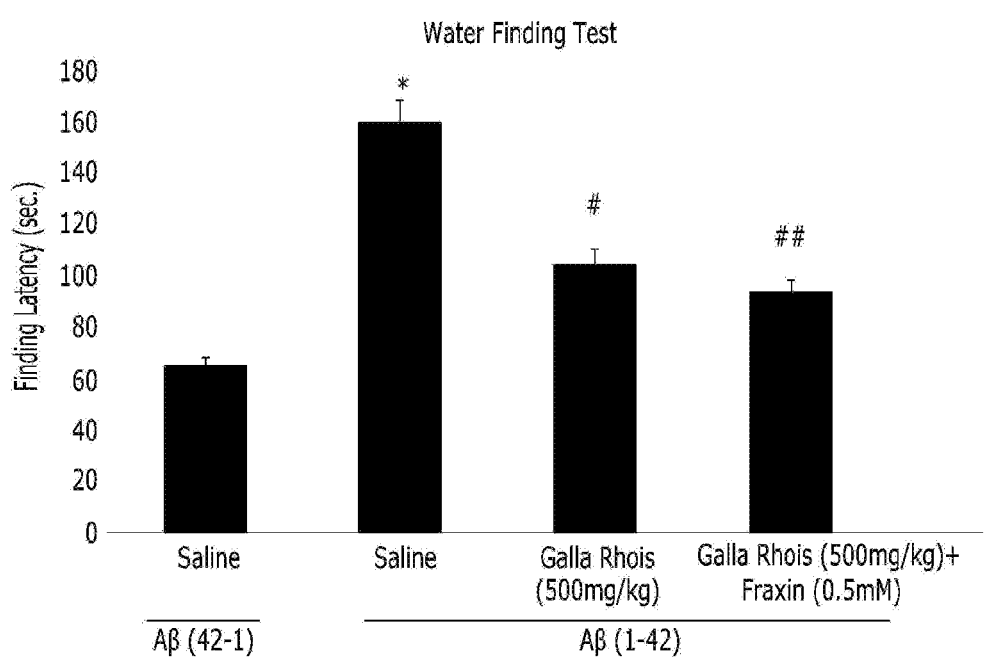

FIG. 11 shows the pharmacological effect of the co-administration of a *Galla rhois* extract and/or fraxin on the cognitive memory (evaluated by the finding latency of a water finding test) of APPswe/PS1dE9 double-expressing mice. Each value is expressed as mean±SEM of 10 mice. #P<0.05, and ##P<0.01 vs. Saline (using one-way ANOVA and a Fisher's PLSD test for a post-test).

Figure 12:
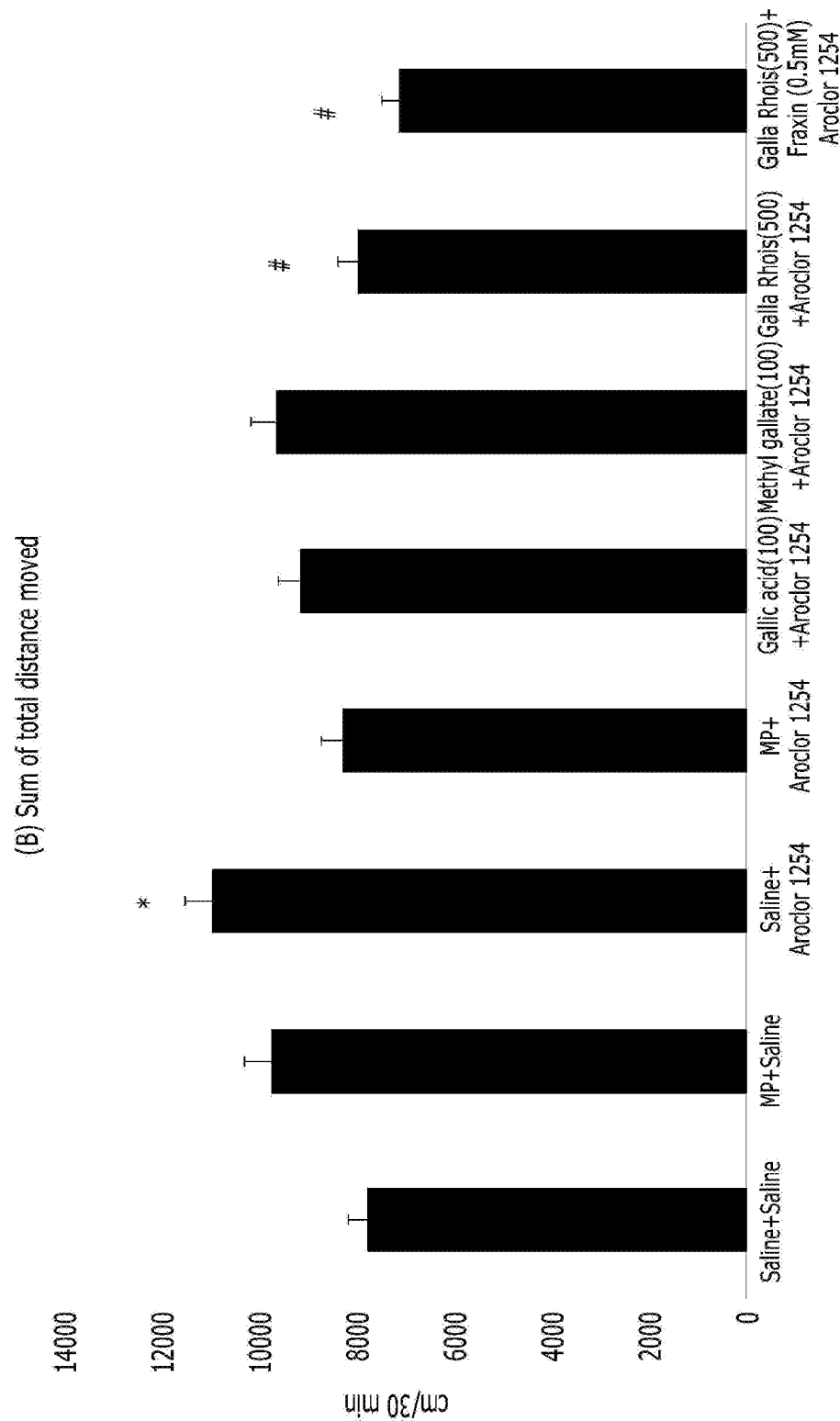

FIG. 12 is a graph showing the effect of *Galla rhois* and/or fraxin on Aroclor 1254-induced hyperlocomotor activity in mice. Each value is expressed as mean±SEM of 12 mice, *P<0.05, **P<0.01 vs. Sal+Sal, and #P<0.05, and ##P<0.01 vs. Sal+Aroclor 1254.

Figure 13:
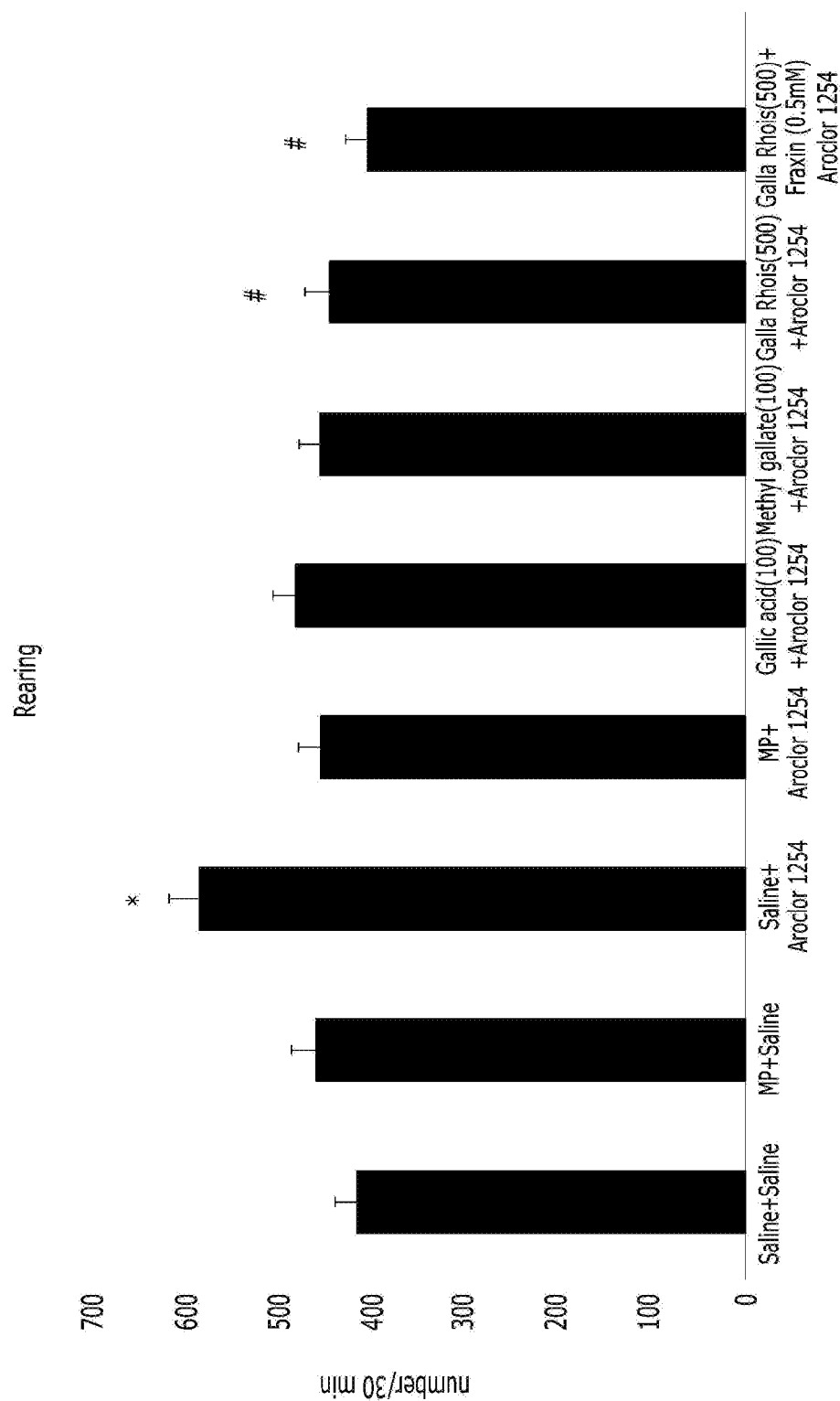

FIG. 13 is a graph showing the effect of *Galla rhois* and/or fraxin on the increase in Aroclor 1254-induced rearing number in mice. Each value is expressed as mean±SEM of 12 mice, *P<0.05 vs. Sal+Sal, and #P<0.05 vs. Sal+Aroclor 1254 (One-way ANOVA is accompanied by a Fisher's PLSD test).

Figure 14:
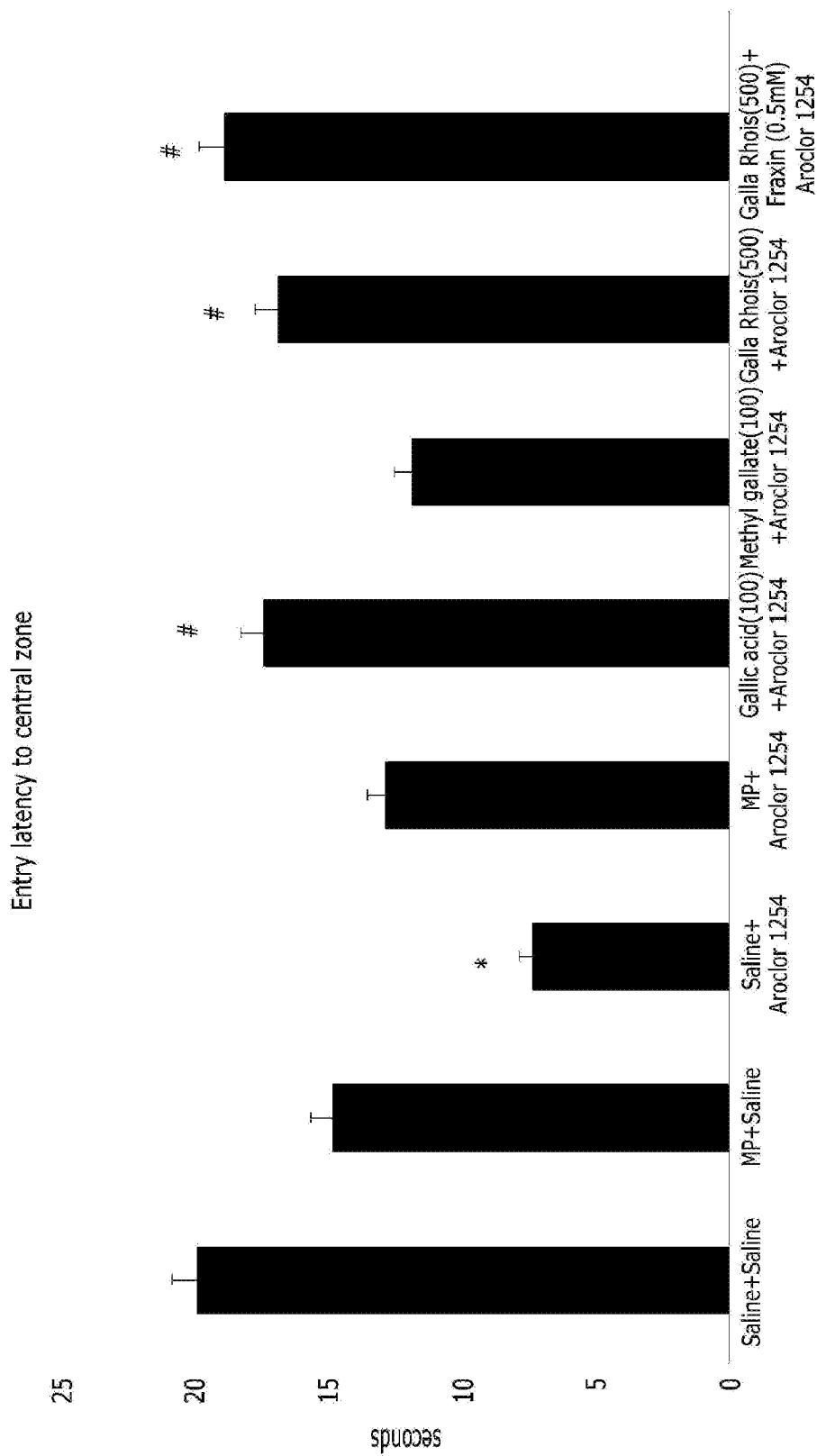

FIG. 14 is a graph showing the effect of *Galla rhois* and/or fraxin on a Aroclor 1254-induced change with respect to entry latency into the central zone in mice. Each value is expressed as mean±SEM of 12 mice, *P<0.01 vs. Sal+Sal, and #P<0.05 vs. Sal+Aroclor 1254 (One-way ANOVA is accompanied by a Fisher's PLSD test).

Figure 15:
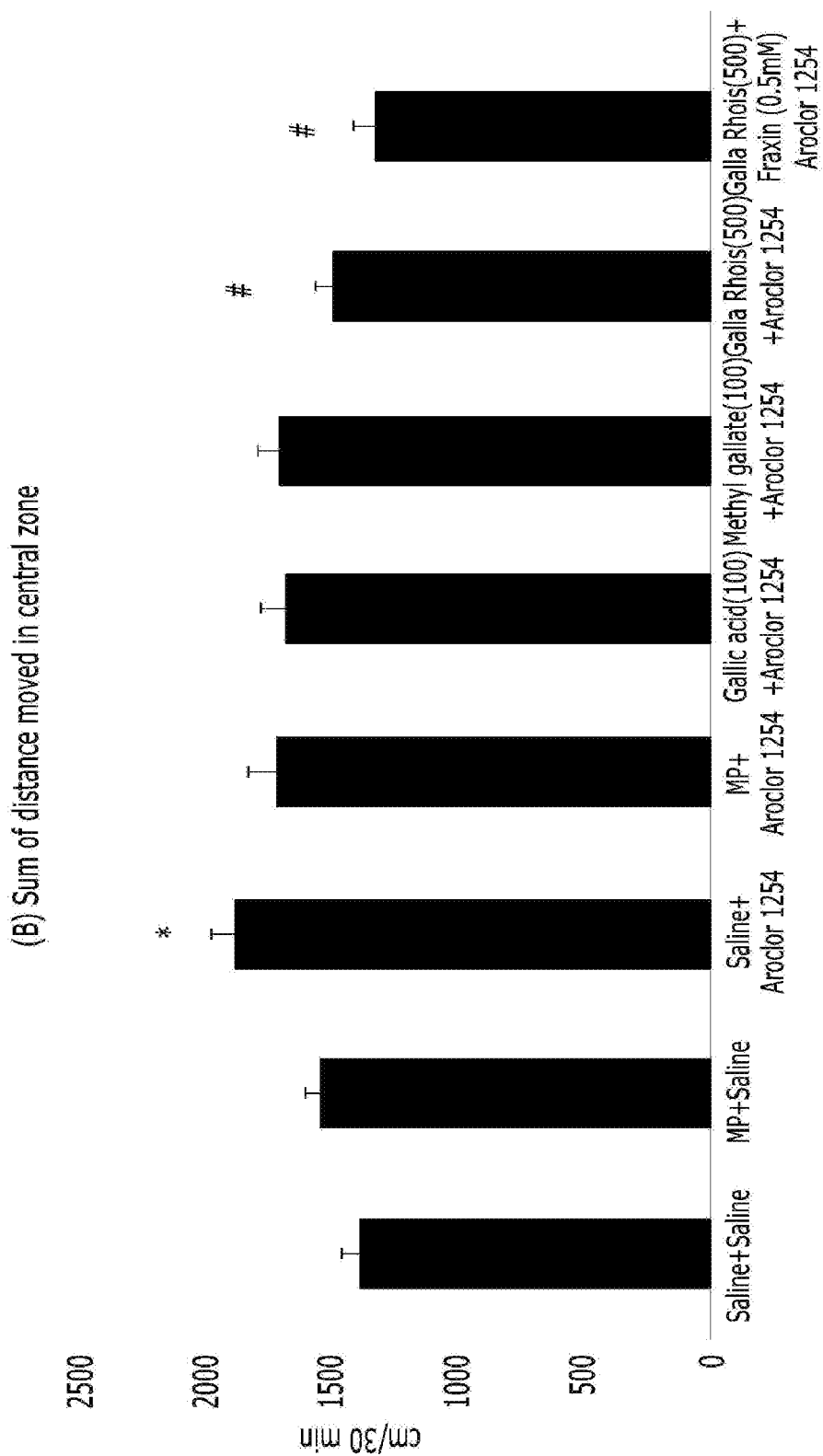

FIG. 15 is a graph showing the effect of *Galla rhois* and/or fraxin on an Aroclor 1254-induced increase with respect to a distance moved in the central zone. Each value is expressed as mean±SEM of 12 mice, *P<0.01 vs. Sal+Sal, #P<0.05, and ##P<0.05 vs. Sal+Aroclor 1254.

Figure 16:
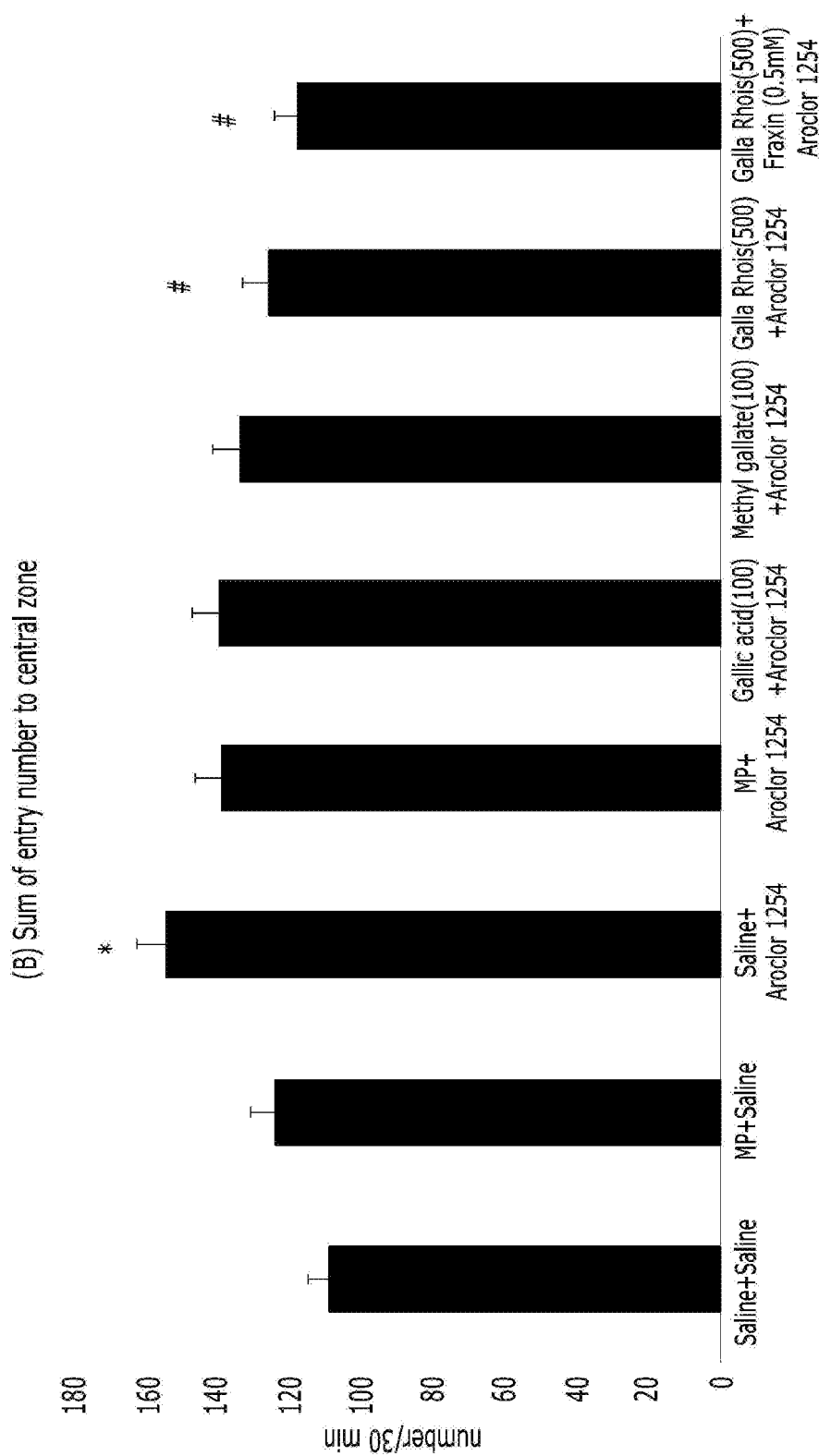

FIG. 16 is a graph showing the effect of *Galla rhois* and/or fraxin on a Aroclor 1254-induced increase with respect to the number of entries into the central zone in mice. Each value is expressed as mean±SEM of 12 mice, *P<0.01 vs. Sal+Sal, and #P<0.05 vs. Sal+Aroclor 1254.

Figure 17:
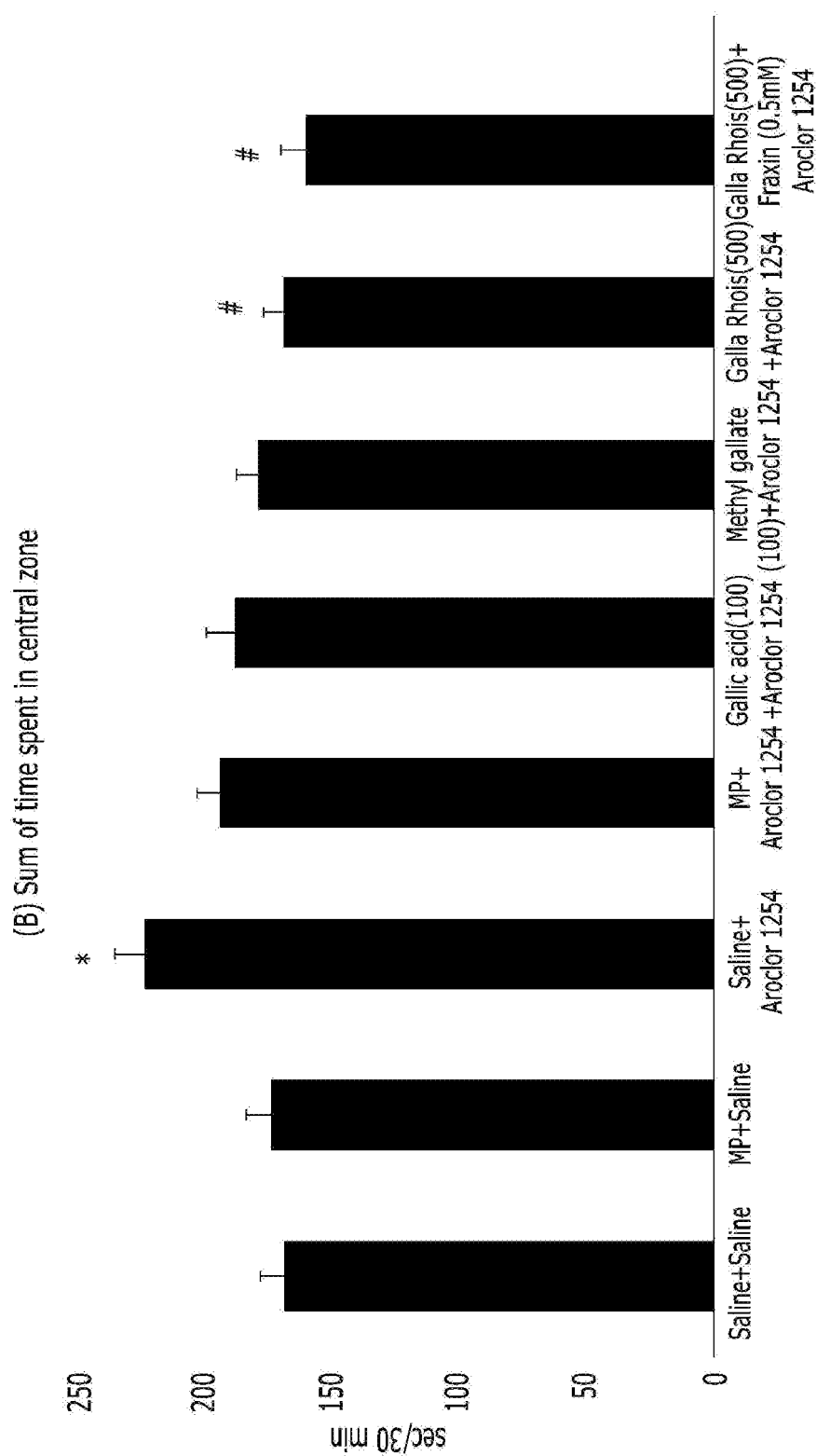

FIG. 17 is a graph showing the effect of *Galla rhois* and/or fraxin on Aroclor 1254-induced change with respect to the time spent in the central zone in mice. Each value is expressed as mean±SEM of 12 mice, *P<0.05 vs. Sal+Sal, and #P<0.05 vs. Sal+Aroclor 1254.

Figure 18:
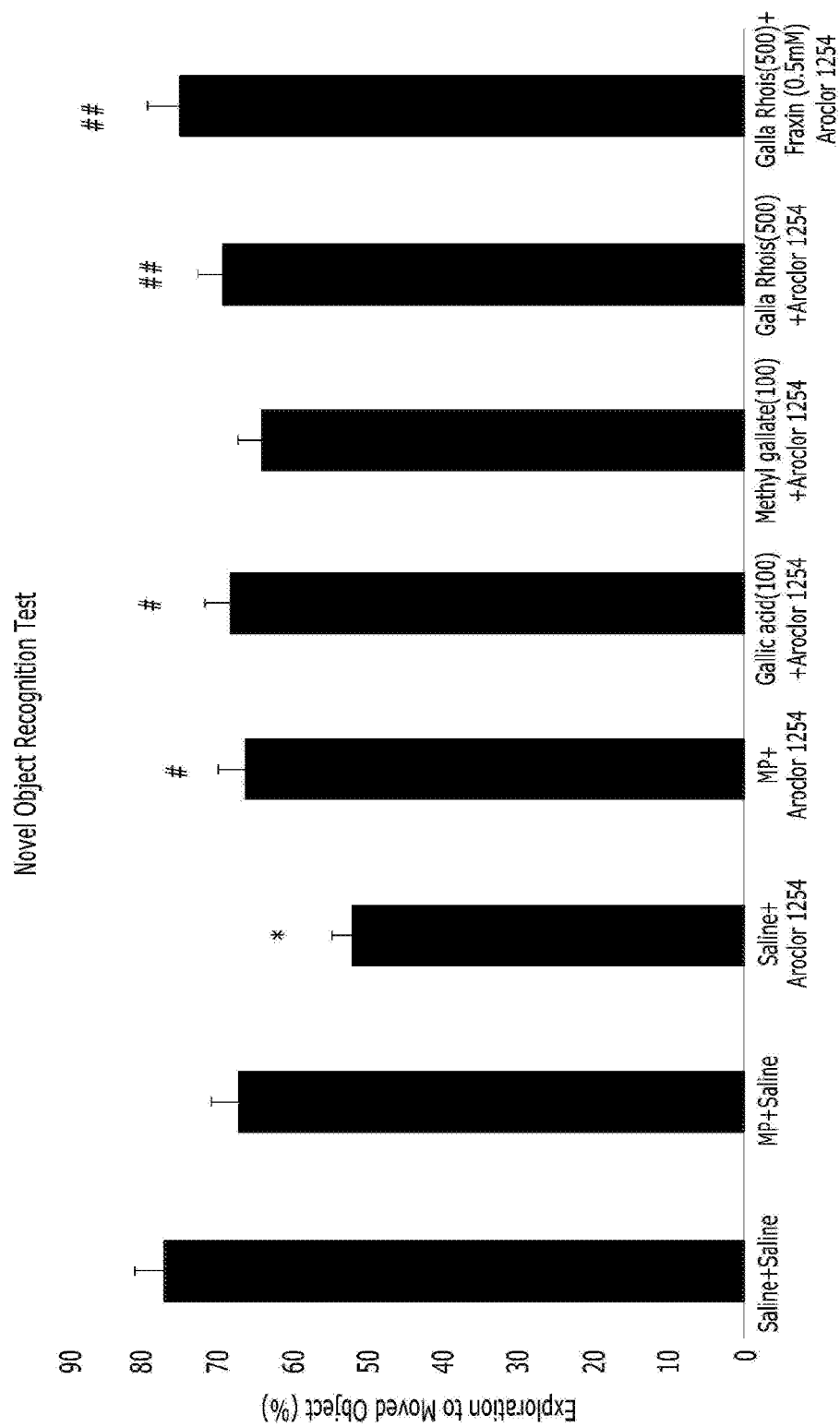

FIG. 18 is a graph showing the effect of *Galla rhois* and/or fraxin on Aroclor 1254-induced learning and memory damage in a novel object recognition test in mice. Each value is expressed as mean±SEM of 12 mice, * P<0.01 vs. Sal+Sal, #P<0.05, and ##P<0.05 vs. Sal+Aroclor 1254 (One-way ANOVA is accompanied by a Fisher's PLSD test).

DETAILED DESCRIPTION

Hereinafter, the present invention will be described in further detail through non-limiting examples.

Example: Preparation of *Galla rhois* Extract and Process of Selecting Fraxin 5 kg of *Galla rhois* (K P) was carefully selected, roughly cut according to the cutting degree and powder degree of the general rules of the pharmacopoeia, and the herbal medicine was weighed and put into an extractor, and extracted with 8 to 10-fold 95% ethanol twice for 5 to 6 hours in a stirring extractor. The resulting extract was filtered through a 1-μm microfilter, and then the filtrate was concentrated under reduced pressured at 50° C. or less and dried, thereby obtaining a 2.39 kg of dry extract (yield: 47.8%).

Components with known antioxidant activity were provided, and it was determined that gallic acid and fraxin have the highest activity through antioxidant activity screening.

Compounds used in the antioxidant activity screening of the present invention are A1 to A7 below:

A1. A flavonoid compound of quercetin-3-O-β-D-glucuronopyranoside, A2. A phenylpropanoid compound of 1-O-caffeoyl-Quercetin-3-O-β-D-glucopyranoside, A3. A coumarin compound of fraxin, A4. A tannin compound of methyl gallate (gallicin), A5. A flavonoid compound of 2"-O-rhamnosylvitexin, A6. A depside-type phenylpropanoid compound of Acteoside, and A7. A benzyl alcohol-related compound of 1,3-bis[4-(β-D-glucopyranosyl)benzyl]citrate Human umbilical vein endothelial cells (HUVECs) were treated with each of the 7 types of antioxidants A1-A7, and then an oxidant, hydrogen peroxide, was administered to analyze the degree of cell damage by an MTT assay, and then the activity of superoxide dismutase and catalase was measured.

As a result of the experiment, A6 and A7 did not show an ROS scavenging effect or a cell regeneration effect. A4 has high ROS scavenging effect and cell regeneration effect, whereas A3 has a high cell regeneration effect, but has a poor ROS scavenging effect, it is considered that the antioxidant effect of A3 is caused by a mechanism different from that of ROS scavenging.

Superoxide dismutase (SOD), catalase assay: The activity of both enzymes that have an effect of eliminating ROS generated in cells or entering from the outside was not greatly changed by $H_2O_2$ treatment, but when A3 was treated before $H_2O_2$ treatment, an increase in SOD activity could be observed.

Lipid peroxidation (LPO) assay: LPO tends to slightly increase as cells age. Particularly, when cells were exposed to $H_2O_2$, it could be seen that the LPO result increases an MDA amount, and it was confirmed that such increase is greatly reduced by A3 and A4 treatment, and this activity was not observed with A1, A2 and A5 to A7.

Figure 1:
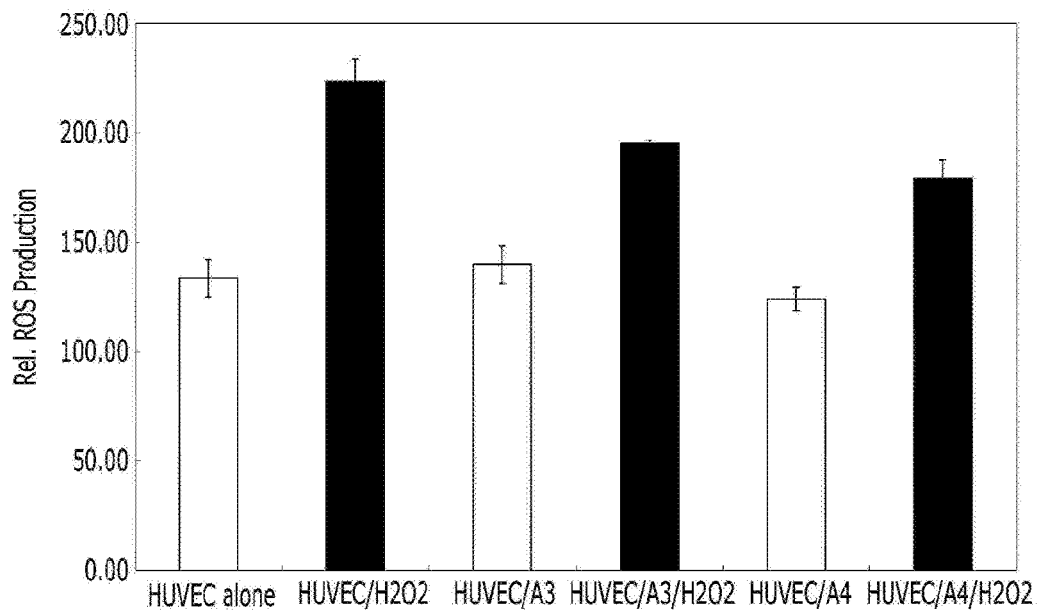
FIG. 1 is a graph showing a change in intracellular ROS level by phytochemical treatment.

Production of reactive oxygen species (ROS): To measure ROS generated in cells, DCF fluorescence was used. It was observed that an ROS level in $H_2O_2$-treated HUVECs increases by 55% compared to those not treated with $H_2O_2$, and it was seen that this increase is reduced by 39% and 24% when A3 and A4 were added (FIG. 1).

Therefore, the inventors selected A3 and A4 from among the A1 to A7 compounds as a candidate to be combined with a *Galla rhois* extract, and since the *Galla rhois* extract contains a large amount of methyl gallate, which is the A4 compound, an effect of the *Galla rhois* extract to which A3, fraxin, is added, not A4, was to be evaluated.

In the present invention, the experiment was carried out with fraxin having a concentration of 0.5 mM, and this concentration is a result of performing an experiment of the free radical-scavenging activity of fraxin using a DPPH assay. A DPPH solution was treated with various concentrations of fraxin (0.02, 0.1 and 0.5 mM), and a change in absorbance was monitored at 517 nm for 10 minutes. The free radical scavenging activity was approximately 10%, 18% or 50% at the fraxin concentration of 0.02, 0.1 or 0.5 mM, respectively, and 0.5 mM was selected for subsequent experiment.

Experimental Example 1: Evaluation of Pharmacological Efficacy of *Galla rhois* Extract and/or Fraxin in Alzheimer's Disease Model 1) An Aβ-mediated decline in cognitive memory was evaluated in 12-week-old mice. ICR mice [Orient Bio Inc., Gyeonggi, Korea] were purchased and acclimated in a laboratory animal cage for 1 week, followed by performing drug administration and cognitive memory evaluation. 400 pmol of toxic Aβ (1-42) (American Peptide Company, Sunnyvale, Calif., USA) or non-toxic Aβ (42-1) (American Peptide Company, Sunnyvale, Calif., USA) as a control was administered into the third ventricle. The cognitive memory evaluation was performed from 3 days after Aβ administration. A *Galla rhois* ethanol extract (500 mg/kg, p.o.) and/or fraxin (0.5 mM) were/was orally administered once a day from two days before Aβ administration until the end of the cognitive memory evaluation. During the cognitive memory evaluation, to prevent the direct effects of the drugs on behavior, the drugs were administered after the behavioral and cognitive function evaluations were completed.

2) Drug administration to amyloid precursor protein/presenilin-1 (APPswe/PS1dE9) double-expressing mice, which are Alzheimer's models In this experiment, 6-month-old APPswe/PS1dE9 double-expressing mice (Jackson Laboratory, Bar Harbor, Mass., USA) were used. A *Galla rhois* ethanol extract (500 mg/kg, p.o.) and/or fraxin (0.5 mM) were/was orally administered to the APPswe/PS1dE9 double-expressing mice once a day for 3 months, followed by performing cognitive memory evaluation. During the cognitive memory evaluation, to prevent the direct effects of the drugs on behavior, the drugs were administered after the behavioral and cognitive function evaluations were completed. One day after cognitive memory evaluation was completed, the animals were sacrificed to evaluate the degree of Aβ accumulation.

Cognitive Memory Evaluation Methods (1) Y-Maze Test

The Y-maze has three arms configured in a Y shape, in which each arm is formed with a black plastic box with a size of 25 cm (length)×14 cm (height)×5 cm (width). A mouse was placed at the end of one arm and allowed to move freely in the arm for 8 minutes. The number of entries of the mouse into each arm was recorded with a video camera. The evaluation index for the alternation behavior was determined as obtaining 1 point when the mouse enters into all three arms, and was compared with a control. The alternation score of the mouse was expressed by dividing the actual scores obtained by the mouse by possible alternation scores and converting the result value to 100%.

(2) Novel Object Test

On the first day, a mouse was placed in a box of 40 cm×40 cm×30 cm and acclimated by allowing it to move freely for 10 minutes. On the second day, two objects were placed in the box and then the reaction time for each object was recorded. After 24 hours, one of the two objects was replaced with a novel object, and the reaction time for the novel object was recorded.

(3) Water Finding Test

The water finding test is a method of evaluating latent learning and attentional spatial memory, in which, on the first day, a mouse was allowed to recognize the position of a nozzle of a water bottle in the apparatus, and after 24 hours of being deprived of water, the mouse was placed again in the apparatus to find the nozzle of the water bottle, followed by measuring the time (finding latency). However, on the second day, the position of the water bottle and the length of the nozzle were slightly modified to make the mouse find a new position with attention based on the information learned on the first day.

(4) Passive Avoidance Test

An apparatus for the passive avoidance test consists of two rooms, and there was a guillotine door between the two rooms. A shock generator was disposed on the floor of each room. On the first day, in an acquisition trial, the mouse was placed in one of the two rooms and acclimated for 15 seconds, a light was turned on in the room in which there was the mouse and the guillotine door opened. As the mouse moved from the bright room to the dark room, the guillotine door closed and an electric shock (0.5 mA, 5 s) was applied to the floor of the dark room. On the second day, the mouse was placed in the same apparatus, and the time to move from the bright room to the dark room was measured (step-through latency).

(5) Morris Water Maze Test

A water bath for evaluating a water maze is a cylindrical water bath with a size of 97 cm (diameter)×60 cm (height). During the test, the water bath was filled with powdered milk diluted with 23±2° C. water. A transparent platform was installed 2 cm below the water surface in the water bath, and four signs were placed on the outside of the water bath. The motion trajectory of a mouse was analyzed through a video tracking system (EthoVision, Noldus, The Netherlands).

(5-1) Reference Memory Test

During each trial, a mouse was placed in a water bath without facing a platform at a position where five starting points were randomly selected. In each trial, the mouse was placed in the water bath, the time to find the platform (escape latency) was recorded, when the mouse found the platform, it was allowed to stand on the platform for 10 seconds and then transferred to a home cage. When the mouse did not find the platform within 60 seconds, the escape latency was recorded to be 60 seconds. Each trial was carried out four times a day for 4 days (3rd day to 6th day) from three days after β-amyloid administration.

(5-2) Probe Test

Seven days after β-amyloid administration, a probe test was performed. After the platform was removed, a mouse was allowed to swim in a water bath for 60 seconds, and how many times the mice passed the position at which the platform had been placed while swimming was recorded.

(5-3) Working Memory Test

A working memory test was carried out on 8th day to 10th day after β-amyloid administration. This test is similar to the reference memory test, but the escape latency was measured by changing the position of the platform every day. Five trials were conducted a day, and the escape latencies of the $2^{nd}$ to $5^{th}$ trials were used.

Results of said animal effect test are as follows.

Figure 2:
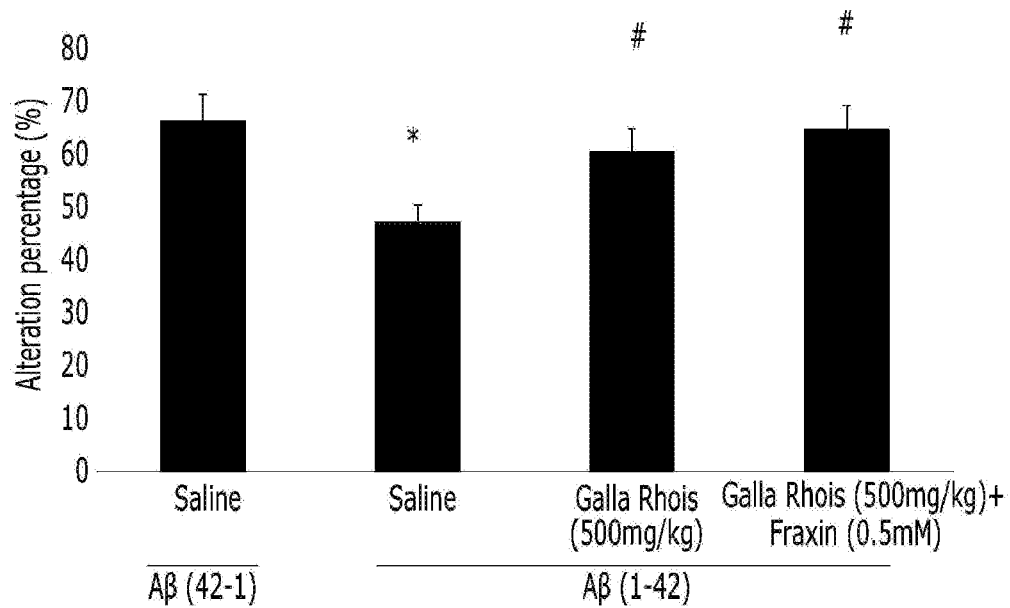
FIG. 2 shows the effect of co-administration of a *Galla rhois* ethanol extract and/or fraxin on a β-amyloid (1-42)-mediated decline in cognitive memory. The cognitive memory was measured by alternation behavior of a Y-maze test. The experiment was carried out with 16 mice per group, and each value is expressed as mean±SEM. *$P<0.01$ vs. Saline+β-amyloid (42-1), and #$P<0.05$ vs. Saline+β-amyloid (1-42) (using one-way ANOVA and a Fisher's PLSD test for a post-test).

Cognitive Memory Improving Effect of *Galla rhois* Extract and Fraxin on Decline in Spatial Short-Term Memory Induced by β-Amyloid (1-42) Administration β-amyloid (1-42) administration significantly reduced alternation behavior in the Y-maze. The *Galla rhois* extract significantly inhibited a decrease in alternation behavior due to β-amyloid (1-42) (FIG. 2). In addition, in the co-administration of the *Galla rhois* extract and fraxin, compared to the single administration of *Galla rhois*, a significant increase of approximately 6.66% in alternation behavior was shown.

Figure 3:
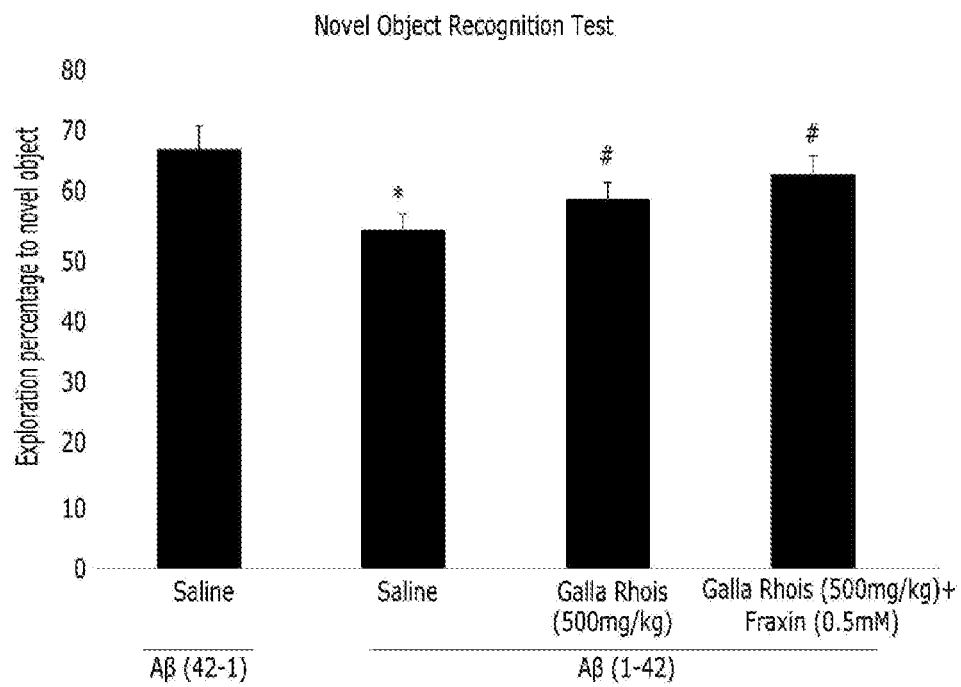
FIG. 3 shows the effect of co-administration of a *Galla rhois* ethanol extract and/or fraxin on a β-amyloid (1-42)-mediated decline in cognitive memory. The cognitive memory was measured using a novel object recognition test. The experiment was carried out with 16 mice per group, and each value is expressed as mean±SEM. *$P<0.01$ vs. Saline+β-amyloid (42-1), and #$P<0.05$ vs. Saline+β-amyloid (1-42) (using one-way ANOVA and a Fisher's PLSD test for a post-test).

Effect of *Galla rhois* Extract and Fraxin on Decline in Visual Recognition Memory Induced by β-Amyloid (1-42) Administration The β-amyloid (1-42) administration significantly decreased exploration for a novel object in a novel object recognition test. The *Galla rhois* extract significantly inhibited a decrease in exploration for a novel object by β-amyloid (1-42) (FIG. 3). In addition, in the co-administration of the *Galla rhois* extract and fraxin, compared with the single administration of *Galla rhois*, the decrease in exploration for a novel object caused by β-amyloid (1-42) was inhibited more significantly, by approximately 6.78% (FIG. 3).

Figure 4:
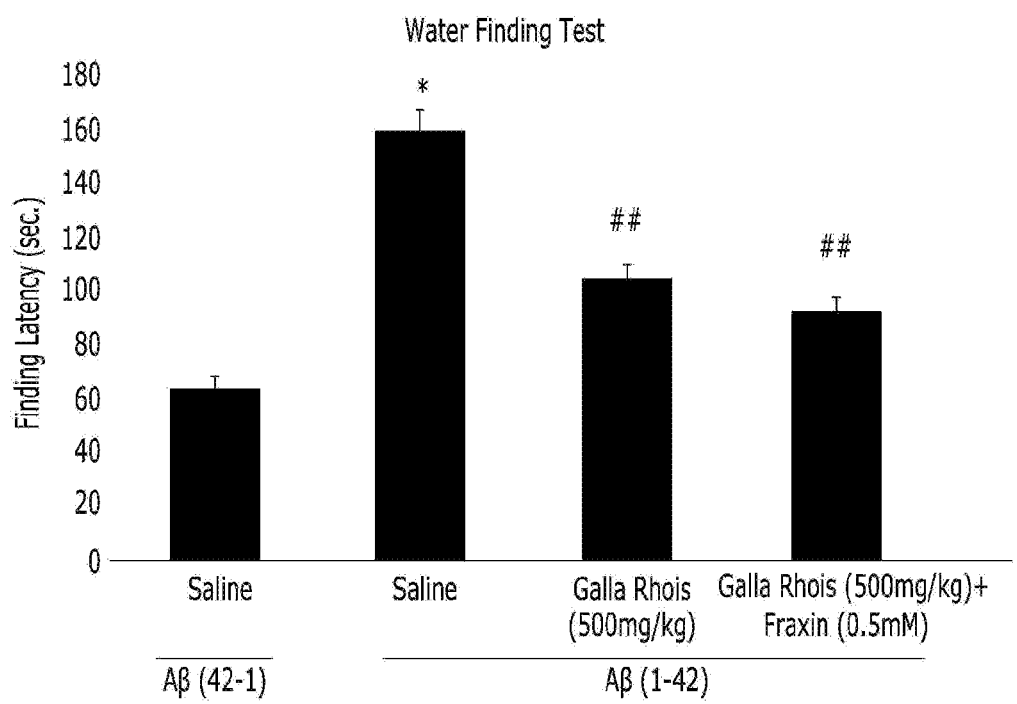
FIG. 4 shows the effect of co-administration of a *Galla rhois* ethanol extract and/or fraxin on a β-amyloid (1-42)-mediated decline in cognitive memory. The cognitive memory was measured by observing the finding latency of a water finding test. The experiment was carried out with 16 mice per group, and each value is expressed as mean±SEM. *$P<0.01$ vs. Saline+β-amyloid (42-1), and #$P<0.05$, ##$P<0.01$ vs. Saline+β-amyloid (1-42) (using one-way ANOVA and a Fisher's PLSD test for a post-test).

Cognitive Memory Improving Effect of *Galla rhois* Extract and Fraxin on Decline in Latent Learning Induced by β-Amyloid (1-42) Administration The β-amyloid (1-42) administration significantly increased finding latency in a water finding test that evaluates latent learning. The *Galla rhois* extract significantly inhibited an increase in finding latency by β-amyloid (1-42) (FIG. 4). In addition, in the co-administration of the *Galla rhois* extract and fraxin, compared with the single administration of *Galla rhois*, the increase in finding latency caused by β-amyloid (1-42) was inhibited more significantly, by approximately 11.43% (FIG. 4).

Figure 5:
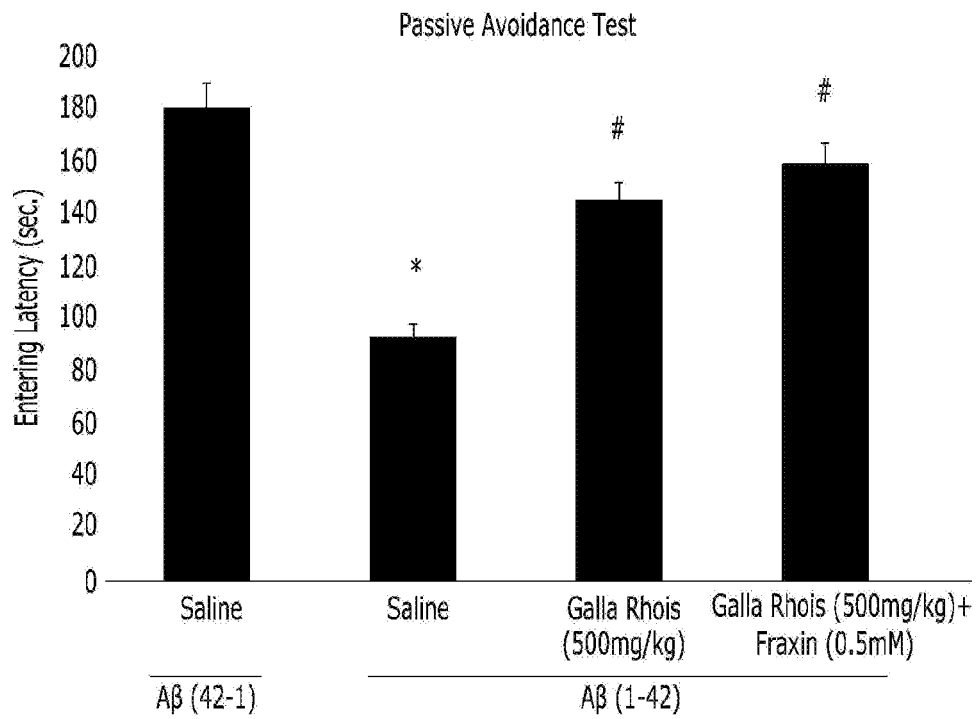
FIG. 5 shows the effect of co-administration of a *Galla rhois* ethanol extract and/or fraxin on a β-amyloid (1-42)-mediated decline in cognitive memory. The cognitive memory was measured by observing the step-through latency of a passive avoidance test. The experiment was carried out with 16 mice per group, and each value is expressed as mean±SEM. *$P<0.01$ vs. Saline+β-amyloid (42-1), and #$P<0.05$ vs. Saline+β-amyloid (1-42) (using one-way ANOVA and a Fisher's PLSD test for a post-test).

Cognitive Memory Improving Effect of *Galla rhois* Extract and Fraxin on Decline in Fear Learning and Memory Induced by β-Amyloid (1-42) Administration The β-amyloid (1-42) administration significantly decreased step-through latency in a passive avoidance test that evaluates fear learning and memory. The *Galla rhois* extract significantly inhibited the decrease in step-through latency caused by β-amyloid (1-42) (FIG. 5). In addition, in the co-administration of the *Galla rhois* extract and fraxin, compared with the single administration of *Galla rhois*, the decrease in step-through latency caused by β-amyloid (1-42) was inhibited more significantly, by approximately 10.34% (FIG. 5).

Figure 6:
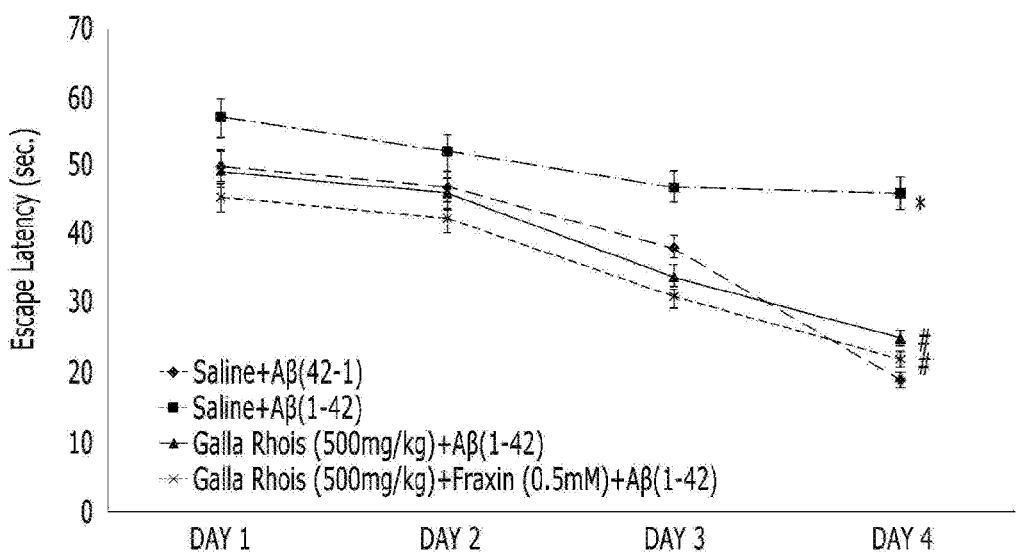
FIG. 6 shows the effect of co-administration of a *Galla rhois* ethanol extract and/or fraxin on a β-amyloid (1-42)-mediated decline in cognitive memory. The cognitive memory was measured using a reference memory test of a Morris water maze. Eight mice per group were measured four times a day, and each value is expressed as mean±SEM. *$P<0.01$ vs. Saline+β-amyloid (42-1), and #$P<0.05$ vs. Saline+β-amyloid (1-42) (using one-way ANOVA for repeated measurement and a Fisher's PLSD test for post-test).
Figure 7:
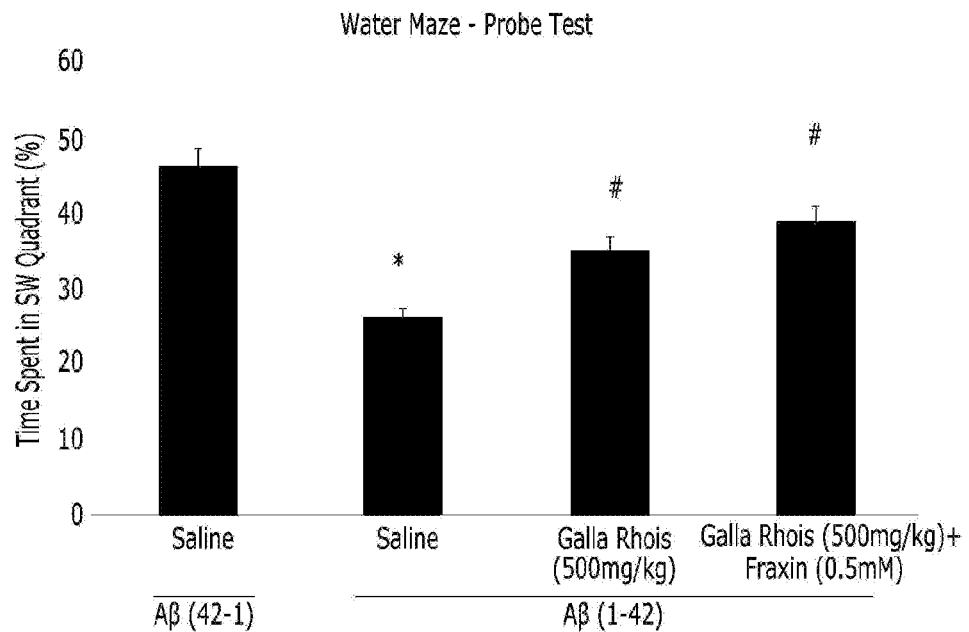
FIG. 7 shows the effect of co-administration of a *Galla rhois* ethanol extract and/or fraxin on a β-amyloid (1-42)-mediated decline in cognitive memory. The cognitive memory was measured using a probe test of a Morris water maze. Eight mice per group were measured twice, and each value is expressed as mean±SEM. *$P<0.01$ vs. Saline+β- amyloid (42-1), and #P<0.05 vs. Saline+β-amyloid (1-42) (using one-way ANOVA and a Fisher's PLSD test for a post-test).

Cognitive Memory Improving Effect of *Galla rhois* Extract and Fraxin on Decline in Spatial Reference Memory Induced by β-Amyloid (1-42) Administration As a result of evaluation through a hidden platform test and a probe test with the Morris water maze, the β-amyloid (1-42) administration significantly induced a decline in spatial reference memory. That is, in β-amyloid (1-42)-administered mice, compared with β-amyloid (42-1)-administered mice, the time to find a safe platform in a water bath was not only significantly increased, but also the time spent in the quadrant in which the platform was placed was significantly decreased in the probe test that performs measurement without the platform. The *Galla rhois* extract significantly inhibited an increase in escape latency and a decrease in time spent in the quadrant in which there is a platform by β-amyloid (1-42) (FIGS. 6 and 7). In addition, in the co-administration of the *Galla rhois* extract and fraxin, compared with the single administration of *Galla rhois*, the increase in escape latency and the decrease in time spent in the quadrant in which there is a platform caused by β-amyloid (1-42) were inhibited more significantly, by approximately 12.00% (FIGS. 6 and 7).

Cognitive Memory Improving Effect of *Galla rhois* Extract and Fraxin on Decline in Spatial Working Memory Induced by β-Amyloid (1-42) Administration The β-amyloid (1-42) administration significantly induced a decline in spatial working memory in a working memory test with the Morris water maze. The *Galla rhois* extract significantly inhibited an increase in escape latency caused by β-amyloid (1-42) (FIG. 8). In addition, in the co-administration of the *Galla rhois* extract and fraxin, compared with the single administration of *Galla rhois*, the increase in escape latency caused by β-amyloid (1-42) was more significantly inhibited by approximately 9.43% (FIG. 8).

Cognitive Memory Improving Effect of *Galla rhois* Extract and Fraxin on Spatial Short-Term Memory in APPswe/PS1dE9 Double-Expressing Mice As a result of a Y-maze test that evaluates short-term spatial memory in APPswe/PS1dE9 double-expressing mice, the *Galla rhois* extract significantly increased alternation behavior (FIG. 9). In addition, in the co-administration of the *Galla rhois* extract and fraxin, compared with the single administration of *Galla rhois*, the alternation behavior was more significantly increased by approximately 10.53% (FIG. 9).

Improving Effect of *Galla rhois* Extract and Fraxin on Visual Recognition Memory in APPswe/PS1dE9 Double-Expressing Mice As a result of performing a novel object recognition test that evaluates visual recognition memory in APPswe/PS1dE9 double-expressing mice, the *Galla rhois* extract significantly increased exploration for a novel object (FIG. 10). In addition, in the co-administration of the *Galla rhois* extract and fraxin, compared with the single administration of *Galla rhois*, exploration was more significantly increased by approximately 9.76% (FIG. 10).

Improving Effect of *Galla rhois* Extract and Fraxin on Latent Learning in APPswe/PS1dE9 Double-Expressing Mice As a result of performing a water finding test that evaluates latent learning in APPswe/PS1dE9 double-expressing mice, the *Galla rhois* extract significantly decreased finding latency (FIG. 11). In addition, in the co-administration of the *Galla rhois* extract and fraxin, compared with the single administration of *Galla rhois*, the finding latency was more significantly decreased by approximately 10.48% (FIG. 11).

Experimental Example 2: Pharmacological Efficacy of *Galla rhois* Extract and/or Fraxin in ADHD Models 1) Laboratory Animals and Drug Treatment Since ADHD is a disease mainly occurring in children, immature mice have to be used in the experiment, and thus ICR mice [Orient Bio, Inc., Gyeonggi, Korea] were purchased and acclimated in a laboratory animal cage, followed by mating. Aroclor 1254 (18 mg/kg) was orally administered into mothers once a day from gestational 6th day to postnatal 21th day. On postnatal 21th day, only male offspring was weaned, and then from the postnatal 21th day until the end of the behavioral test, gallic acid (100 mg/kg, p.o.), methyl gallate (100 mg/kg, p.o.) or the *Galla rhois* extract (500 mg/kg, p.o.) and/or fraxin (0.5 mM) were/was administered into the weaned offspring once a day.

On postnatal 35th day, spontaneous momentum and impulsive tendencies were evaluated using an open field test, and on 36th and 37th days, attention and cognitive memory were evaluated using a novel object recognition test. As a reference drug, methylphenidate was used. Experimental details are shown in FIG. 12.

2) Behavioral Evaluation (1) Open Field Test

A mouse was placed in a block acryl box with a size of 40×40×30 cm, and its behavior was measured for 30 minutes using a video tracking system. An open field was divided into 9 sections, and the central area was set as a central zone. The hyperactivity index of ADHD used spontaneous momentum (distance moved in cm), and the indicators of impulsive behavior were rearing behavior, the time spent in the central zone, the number of entries into the central zone, and the time to first enter the central zone. In open field evaluation, it is known that the time spent in the central zone is long and frequent, and as the first entry time is shorter, there is impulsiveness, and in the opposite case, the mouse has an anxiety symptom. Behavioral measurement was performed between 9 a.m. and 6 p.m.

(2) Novel Object Recognition Test

Twenty-four hours after the open field test, two objects were fixed in an acryl box which was the same as used in the open field test. After a mouse was placed, the time to approach each object was measured for 10 minutes using a video tracking system. After 24 hours, one of the two objects was replaced with a novel object, the mouse was then placed into the box, the time to approach each object was measured for 10 minutes using a video tracking system, and the time to approach the novel object in the time to approach the two objects was calculated and expressed as a percentage.

The result of Example 3 is shown below.

Pharmacological Effect of *Galla rhois* Extract and/or Fraxin on Hyperactivity Induced by Aroclor 1254

Aroclor 1254 administration significantly induced locomotor activity and increased rearing behavior. In the co-administration of the *Galla rhois* extract and fraxin, the increases in hyperlocomotor activity and rearing behavior induced by Aroclor 1254 were remarkably inhibited (FIGS. 12 and 13).

Pharmacological Effect of *Galla rhois* Extract and/or Fraxin on Aroclor 1254-Induced Impulsive Behavior Aroclor 1254 administration significantly increased the time spent in the central zone of an open field and the number of entries into the central zone, and the time of first entry into the central zone was significantly shortened, thereby indicating impulsive behavior. In the co-administration of the *Galla rhois* extract and fraxin, the Aroclor 1254-induced impulsive behavior was remarkably inhibited (FIGS. 14 to 17).

Pharmacological Effect of *Galla rhois* Extract and/or Fraxin on Aroclor 1254-Induced Attention Disorder/Decline in Learning Memory Aroclor 1254 administration significantly reduced the time spent showing interest in a novel object in a novel object recognition test, thereby indicating an attention deficit and a decline in learning memory. In the co-administration of the *Galla rhois* extract and fraxin, the Aroclor 1254-induced attention disorder/decline in learning memory were remarkably inhibited (FIG. 18).

What is claimed is:

1. A method of preventing or treating attention deficit hyperactivity disorder, comprising:
   administering a composition comprising a *Galla rhois* extract and fraxin to a subject with attention deficit hyperactivity disorder or at risk of attention deficit hyperactivity disorder,
   wherein the concentration of the fraxin in the composition is 0.1 to 0.5 mM.

2. The method of claim 1, wherein the concentration of the fraxin in the composition is 0.5 mM.

* * * * *